(12) United States Patent
Hudson et al.

(10) Patent No.: US 8,998,855 B2
(45) Date of Patent: Apr. 7, 2015

(54) SYRINGE AND NEEDLE COVER REMOVER

(75) Inventors: Christopher Hudson, Witney (GB); Clive Nicholls, Stokenchurch (GB)

(73) Assignee: Owen Mumford, Ltd., Woodstock, Oxfordshire (GB)

( * ) Notice: Subject to any disclaimer, the term of this patent is extended or adjusted under 35 U.S.C. 154(b) by 901 days.

(21) Appl. No.: 13/129,418

(22) PCT Filed: Nov. 17, 2009

(86) PCT No.: PCT/GB2009/051557
§ 371 (c)(1),
(2), (4) Date: Oct. 18, 2011

(87) PCT Pub. No.: WO2010/055357
PCT Pub. Date: May 20, 2010

(65) Prior Publication Data
US 2012/0029439 A1 Feb. 2, 2012

(30) Foreign Application Priority Data

Nov. 17, 2008 (GB) .................................. 0820967.8

(51) Int. Cl.
*A61M 5/00* (2006.01)
*A61M 5/32* (2006.01)

(52) U.S. Cl.
CPC ........... *A61M 5/3202* (2013.01); *A61M 5/3204* (2013.01); *A61M 2005/3215* (2013.01)

(58) Field of Classification Search
CPC ....... A61M 5/00; A61M 5/3129; A61M 5/24; A61M 5/2033; A61M 5/3287; A61M 5/32; A61M 5/178
USPC .............................. 604/187, 136, 272, 164.11
See application file for complete search history.

(56) References Cited

U.S. PATENT DOCUMENTS 930,477 A 8/1909 Hudson
3,620,209 A 11/1971 Kravitz
(Continued)

FOREIGN PATENT DOCUMENTS

DE 1049188 1/1959
DE 3730469 6/1988
(Continued)

OTHER PUBLICATIONS

Ascensia® MICROLET® VACULANCE® Lancing Device; product information brochure for Easy Lancing on Alternative Sites; www.bayercarediabetes.com; printed Feb. 13, 2004, 2 pages.
(Continued)

*Primary Examiner* — Scott Medway
(74) *Attorney, Agent, or Firm* — Kilpatrick Townsend & Stockton, LLP

(57) ABSTRACT

Apparatus for loading into an injection device and comprising a syringe and a boot remover. The syringe has a syringe body, a needle and a boot providing a sterile cover for the needle. The boot remover has a body for substantially enclosing the boot and a lip or lips projecting inwardly to engage a junction between the boot and the syringe body. The boot remover also has, at its widest point, substantially the same outer dimension as, or a smaller outer dimension than, the syringe body. The apparatus can be loaded into an injection device through an opening at a distal end of the device such that, when loaded, a portion of the boot remover projects through a proximal end of the device to facilitate removal of the boot remover and boot by a user. This arrangement allows a user to remove the boot from the syringe by holding and pulling on said grip.

6 Claims, 5 Drawing Sheets

(56) References Cited

U.S. PATENT DOCUMENTS

| | | |
|---|---|---|
| 3,698,395 A | 10/1972 | Hasson |
| 4,442,836 A | 4/1984 | Meinecke et al. |
| 4,449,529 A | 5/1984 | Burns et al. |
| 4,462,405 A | 7/1984 | Ehrlich |
| 4,517,978 A | 5/1985 | Levin et al. |
| D281,383 S | 11/1985 | Beach |
| 4,553,541 A | 11/1985 | Burns |
| 4,565,545 A | 1/1986 | Suzuki |
| 4,646,753 A | 3/1987 | Nugent |
| 4,653,513 A | 3/1987 | Dombrowski |
| 4,801,013 A | 1/1989 | Bruno |
| 4,820,287 A | 4/1989 | Leonard |
| RE32,922 E | 5/1989 | Levin et al. |
| 4,858,607 A | 8/1989 | Jordan et al. |
| 4,917,243 A | 4/1990 | Abrams et al. |
| 4,967,763 A | 11/1990 | Nugent et al. |
| 4,998,922 A * | 3/1991 | Kuracina et al. ............. 604/192 |
| 5,011,479 A * | 4/1991 | Le et al. ........................ 604/198 |
| 5,026,388 A | 6/1991 | Ingalz |
| 5,046,612 A | 9/1991 | Mostarda et al. |
| D322,211 S | 12/1991 | Gary |
| 5,104,380 A | 4/1992 | Holman et al. |
| 5,104,388 A | 4/1992 | Quackenbush |
| 5,116,353 A | 5/1992 | Green |
| D327,214 S | 6/1992 | Stuart |
| D327,321 S | 6/1992 | Russell et al. |
| 5,147,306 A | 9/1992 | Gubich |
| 5,154,698 A * | 10/1992 | Compagnucci et al. ...... 604/110 |
| 5,201,324 A | 4/1993 | Swierczek |
| 5,226,895 A | 7/1993 | Harris |
| 5,226,896 A | 7/1993 | Harris |
| 5,242,421 A | 9/1993 | Chan et al. |
| 5,279,585 A | 1/1994 | Balkwill |
| 5,308,340 A | 5/1994 | Harris |
| 5,320,609 A | 6/1994 | Haber et al. |
| 5,324,303 A | 6/1994 | Strong et al. |
| 5,353,806 A | 10/1994 | Heinzelman et al. |
| 5,364,362 A | 11/1994 | Schulz |
| 5,368,047 A | 11/1994 | Suzuki et al. |
| 5,383,865 A | 1/1995 | Michel |
| 5,402,798 A | 4/1995 | Swierczek et al. |
| 5,423,847 A | 6/1995 | Strong et al. |
| 5,439,453 A | 8/1995 | Kashanchi |
| D362,064 S | 9/1995 | Smick |
| 5,454,828 A | 10/1995 | Schraga |
| 5,472,433 A | 12/1995 | Suzuki |
| 5,479,886 A | 1/1996 | Leonard et al. |
| 5,487,748 A | 1/1996 | Marshall et al. |
| 5,514,097 A | 5/1996 | Knauer |
| 5,527,296 A | 6/1996 | Kashanchi |
| 5,547,702 A | 8/1996 | Gleisner |
| 5,552,117 A | 9/1996 | Burns |
| 5,554,166 A | 9/1996 | Lange et al. |
| 5,569,286 A | 10/1996 | Peckham et al. |
| 5,580,794 A | 12/1996 | Allen |
| 5,591,136 A | 1/1997 | Gabriel |
| 5,601,588 A | 2/1997 | Tonomura et al. |
| 5,609,577 A | 3/1997 | Haber et al. |
| 5,613,978 A | 3/1997 | Harding |
| 5,626,566 A | 5/1997 | Petersen et al. |
| 5,628,764 A | 5/1997 | Schraga |
| 5,709,699 A | 1/1998 | Warner |
| 5,725,508 A | 3/1998 | Chanoch et al. |
| 5,730,753 A | 3/1998 | Morita |
| 5,743,889 A | 4/1998 | Sams |
| 5,749,886 A | 5/1998 | Abidin et al. |
| 5,797,942 A | 8/1998 | Schraga |
| 5,827,232 A | 10/1998 | Chanoch et al. |
| 5,837,546 A | 11/1998 | Allen et al. |
| 5,871,494 A | 2/1999 | Simons et al. |
| 5,872,713 A | 2/1999 | Douglas et al. |
| 5,879,311 A | 3/1999 | Duchon et al. |
| 5,879,367 A | 3/1999 | Latterell et al. |
| 5,910,147 A | 6/1999 | Rosenberg et al. |
| 5,916,230 A | 6/1999 | Brenneman et al. |
| 5,951,493 A | 9/1999 | Douglas et al. |
| 6,004,297 A | 12/1999 | Steenfeldt-Jensen et al. |
| D421,214 S | 2/2000 | Koros et al. |
| 6,053,930 A | 4/2000 | Ruppert |
| 6,056,765 A | 5/2000 | Bajaj et al. |
| 6,071,249 A | 6/2000 | Cunningham et al. |
| 6,071,250 A | 6/2000 | Douglas et al. |
| 6,093,156 A | 7/2000 | Cunningham et al. |
| 6,106,539 A | 8/2000 | Fortier |
| 6,132,449 A | 10/2000 | Lum et al. |
| 6,152,942 A | 11/2000 | Brenneman et al. |
| 6,197,040 B1 | 3/2001 | LeVaughn et al. |
| 6,203,504 B1 | 3/2001 | Latterell et al. |
| 6,210,420 B1 | 4/2001 | Mauze et al. |
| 6,248,095 B1 | 6/2001 | Giambattista et al. |
| 6,261,245 B1 | 7/2001 | Kawai et al. |
| D446,107 S | 8/2001 | Carter |
| 6,277,097 B1 | 8/2001 | Klitmose et al. |
| 6,283,982 B1 | 9/2001 | Levaughn |
| 6,306,152 B1 | 10/2001 | Verdonk et al. |
| 6,332,871 B1 | 12/2001 | Douglas et al. |
| 6,419,661 B1 | 7/2002 | Kuhr et al. |
| 6,464,649 B1 | 10/2002 | Duchon et al. |
| 6,491,709 B2 | 12/2002 | Sharma et al. |
| D470,391 S | 2/2003 | Adams |
| 6,558,402 B1 | 5/2003 | Chelak et al. |
| 6,607,508 B2 | 8/2003 | Knauer |
| 6,616,640 B2 | 9/2003 | Chen |
| 6,638,256 B2 * | 10/2003 | Jansen et al. .................. 604/198 |
| 6,645,219 B2 | 11/2003 | Roe |
| 6,706,049 B2 | 3/2004 | Moerman |
| 6,755,805 B1 | 6/2004 | Reid |
| 6,899,698 B2 | 5/2005 | Sams |
| 6,899,699 B2 | 5/2005 | Enggaard |
| 6,902,554 B2 | 6/2005 | Huttner |
| 6,945,961 B2 | 9/2005 | Miller et al. |
| D516,218 S | 2/2006 | Larocca |
| 7,112,187 B2 | 9/2006 | Karlsson |
| D529,792 S | 10/2006 | Klein et al. |
| 7,241,278 B2 | 7/2007 | Moller |
| D553,737 S | 10/2007 | Rolfe |
| 2002/0002354 A1* | 1/2002 | Vetter et al. .................... 604/272 |
| 2002/0013602 A1 | 1/2002 | Huttner |
| 2002/0016606 A1 | 2/2002 | Moerman |
| 2002/0029058 A1 | 3/2002 | Levaughn et al. |
| 2002/0082521 A1 | 6/2002 | Sharma et al. |
| 2002/0130042 A1 | 9/2002 | Moerman et al. |
| 2002/0169393 A1 | 11/2002 | Cunningham et al. |
| 2002/0198444 A1 | 12/2002 | Uchigaki et al. |
| 2003/0050655 A1 | 3/2003 | Roe |
| 2003/0195540 A1 | 10/2003 | Moerman |
| 2004/0098010 A1 | 5/2004 | Davison |
| 2004/0162573 A1 | 8/2004 | Kheiri |
| 2005/0197625 A1 | 9/2005 | Haueter et al. |
| 2006/0100588 A1* | 5/2006 | Brunnberg et al. ........... 604/192 |
| 2007/0129687 A1 | 6/2007 | Marshall et al. |
| 2007/0156163 A1 | 7/2007 | Davison et al. |
| 2007/0162063 A1 | 7/2007 | Marshall et al. |
| 2007/0167916 A1 | 7/2007 | Lee et al. |
| 2007/0265568 A1* | 11/2007 | Tsals et al. ..................... 604/136 |
| 2007/0299394 A1 | 12/2007 | Rolfe et al. |
| 2008/0306446 A1 | 12/2008 | Markussen |
| 2008/0312592 A1* | 12/2008 | Barrow-Williams et al. 604/136 |
| 2009/0054839 A1 | 2/2009 | Moller et al. |
| 2013/0204197 A1* | 8/2013 | Bicknell et al. ............... 604/197 |

FOREIGN PATENT DOCUMENTS

| | | |
|---|---|---|
| EP | 0097748 | 1/1984 |
| EP | 0137975 | 4/1985 |
| EP | 0295075 | 12/1988 |
| EP | 0327910 | 8/1989 |
| EP | 338806 | 10/1989 |
| EP | 0450905 | 10/1991 |
| EP | 0555554 | 8/1993 |
| EP | 0783868 | 7/1997 |
| EP | 897728 | 2/1999 |
| EP | 0925021 | 6/1999 |
| EP | 0956874 | 11/1999 |

(56) References Cited

FOREIGN PATENT DOCUMENTS

| | | |
|---|---|---|
| EP | 1204371 | 5/2002 |
| EP | 1507566 | 11/2003 |
| EP | 1819382 | 8/2007 |
| FR | 2649893 | 1/1991 |
| GB | 2414401 | 11/2005 |
| GB | 2437922 | 11/2007 |
| JP | 10113389 | 5/1998 |
| JP | 2000116777 | 4/2000 |
| WO | 8504089 | 9/1985 |
| WO | 8808724 | 11/1988 |
| WO | 9108786 | 6/1991 |
| WO | 9110460 | 7/1991 |
| WO | 9607443 | 3/1996 |
| WO | 9704707 | 2/1997 |
| WO | 9708986 | 3/1997 |
| WO | 9806331 | 2/1998 |
| WO | 9938554 | 8/1999 |
| WO | 0113794 | 3/2001 |
| WO | 0128423 | 4/2001 |
| WO | 0162150 | 8/2001 |
| WO | 0172361 | 10/2001 |
| WO | 0195806 | 12/2001 |
| WO | 0209575 | 2/2002 |
| WO | 0230495 | 4/2002 |
| WO | 02053214 | 7/2002 |
| WO | 03097133 | 11/2003 |
| WO | 2004002556 | 1/2004 |
| WO | 2004093940 | 11/2004 |
| WO | 2006045526 | 5/2006 |
| WO | 2006045528 | 5/2006 |
| WO | 2006045529 | 5/2006 |
| WO | 2007036676 | 4/2007 |
| WO | 2007047200 | 4/2007 |
| WO | WO2007047200 * | 4/2007 .............. A61M 5/32 |
| WO | 2007132353 | 11/2007 |

OTHER PUBLICATIONS

Search Report dated Feb. 14, 2007 in Application No. GB0600523.5.
Ascensia® MICROLET® VACULANCE® Lancing Device; product information brochure, www.bayercarediabetes.com; printed Feb. 13, 2004, 3 pages.
At Last™ Blood Glucose System User's Manual, AMIRA (c) 1999, 35 pages.
Autopen™ Owen Mumford Ltd., Ltd. of Woodstock, UK, one page (http://www.owenmumford.com, May 7, 2007.
JP 2005185712A Shiga Moulding, WPI Abstract Accession No. 2005-464425 and EPO DOC Abstract.
TheraSense™ The Technology of Caring Owner's Booklet. 35 pages (2000).
"Vacuum-Assisted Lancing of the Forearm: An Effective and Less Painful Approach to Blood Glucose Monitoring," David D. Cunningham, *Diabetes Technology & Therapeutics*, 2(4):541-548 (2000).
Apkarian, et al., "Heat-induced Pain Diminishes Vibrotactile Perception: A Touch Gate," *Somatosens Mot. Res.*, 11(3):259-67 (1994).
Melzack, 'From the Gate to the Neuromatrix,' *Pain Supplement* 6 S121-S126, Published by Elsevier Science B.V. (1999).
Office Action dated Oct. 29, 2010 in European Patent Application No. 05738600.5.
Barnhill, et al., "Using Pressure to Decrease the Pain of Intramuscular Injections", *Journal of Pain and Symptom Management*, Published by Elevier, New York, 12:52-58 (1996).
Davis, "Opening Up the Gate Control Theory", *Nurs. Stand*, 7(45)25-7 (1993).
Search Report dated Sep. 6, 2004 in Application No. GB0409354.8.
Office Action dated Dec. 12, 2006 in U.S. Appl. No. 29/240,920.
Response dated Apr. 16, 2007 in U.S. Appl. No. 29/240,920.
Notice of Allowance dated May 16, 2007 in U.S. Appl. No. 29/240,920.
Supplemental Notice of Allowance dated Aug. 21, 2007 in U.S. Appl. No. 29/240,920.
Issue Notification dated Oct. 23, 2007 in U.S. Appl. No. 29/240,920.
Office Action dated Nov. 27, 2009 in U.S. Appl. No. 11/587,411.
Response dated Apr. 27, 2010 in U.S. Appl. No. 11/587,411.
Office Action dated Aug. 3, 2010 in U.S. Appl. No. 11/587,411.
Response dated Oct. 4, 2010 in U.S. Appl. No. 11/587,411.
Advisory Action dated Oct. 26, 2010 in U.S. Appl. No. 11/587,411.
Response dated Jan. 3, 2011 in U.S. Appl. No. 11/587,411.
Office Action dated Mar. 31, 2011 in U.S. Appl. No. 11/587,411.
Response dated Aug. 31, 2011 in U.S. Appl. No. 11/587,411.
Office Action dated Oct. 27, 2011 in U.S. Appl. No. 11/587,411.
Response dated Jan. 27, 2012 in U.S. Appl. No. 11/587,411.
Advisory Action dated Feb. 6, 2012 in U.S. Appl. No. 11/587,411.
International Search Report and Written Opinion dated Mar. 31, 2010 in Application No. PCT/GB2009/51557.
Search Report dated Mar. 2, 2009 in priority Application No. GB0820967.8.
Glucolet® Automatic Lancing Device / An Illustrated User Procedure, 2 pages (Date Unknown).

\* cited by examiner

SYRINGE AND NEEDLE COVER REMOVER

CROSS REFERENCE TO RELATED APPLICATIONS

This application is the U.S. national phase of International Application No. PCT/GB2009/051557 filed on Nov. 17, 2009 and published in English on May 20, 2010 as International Publication No. WO 2010/055357 A1, which application claims priority to Great Britain Patent Application No. 0820967.8 filed on Nov. 17, 2008, the contents of both of which are incorporated herein by reference.

TECHNICAL FIELD

The present invention relates to syringes with syringe needle cover removers and to injection devices incorporating the same.

BACKGROUND

Various types of injection devices are available for assisting with the injection of a medicament into a patient (human or animal), and which are configured to receive a standard, pre-filled glass or plastic syringe tipped with an injection needle. These devices may have a dose setting mechanism and a main drive spring for driving a plunger into the syringe so as to expel the medicament out through the needle. Injection devices may comprise a further spring for driving the needle out of the device housing into the patient's skin, prior to activation of the main drive spring to expel the medicament.

In order to maintain sterility prior to use, and to avoid "sticking" injuries, the pre-filled syringe is supplied to the injection device assembler with a rubber or plastic sheath or "boot" covering the needle. The boot has an interior space for containing the needle, and a sealing end that abuts the adjacent end of the syringe body to seal that inner space. Immediately prior to use, a user (e.g. healthcare professional or patient) must remove the boot to uncover the needle. This is typically achieved using a boot removal tool that is inserted by a user into the injecting end of the device. The tool comprises a set of sprung fingers that ride over and along the boot as the tool is pushed into the device. The fingers then snap into the junction between the syringe end and the boot. The user can the pull out the tool, bringing the cap with it.

Particularly in the case of expensive medicaments, it is extremely important to minimise the failure rate of assembled injection devices. Considering the boot removal solution outlined in the previous paragraph, it may be difficult to achieve exactly the right degree of flexibility in the fingers to ensure that they can ride over the boot whilst still providing sufficient force to close over the junction at the rear of the boot.

WO 2007/036676 (Cilag GmbH International) discloses an auto injection device comprising a housing and a threaded, removable, protective cap at the injection end of the device. In place, the cap envelopes and closes off the device housing, as well as preventing a delivery locking mechanism on the device from being released. The cap engages with the boot such that removal of the cap also serves to remove the boot, thereby exposing the needle, whilst at the same time releasing the device's locking mechanism. The device is assembled by positioning the cap at the injection end of the device housing and then inserting the syringe and boot into the device. The cap is of greater diameter than the device housing in order to enable it to enclose the injection end of the device.

WO 2007/047200 (Eli Lilly & Co.) provides an injection device comprising a housing and an outwardly-flared needle cap. The needle cap engages with a needle shield or boot on the syringe needle, gripping the boot and allowing it to be removed. The cap is provided with a flat base, allowing the assembled device to be stood upright on a workbench, for instance. To assist this, the cap is flared outwards from the plane of the device housing to provide greater stability.

Further injection devices comprising a housing and boot remover are disclosed in WO 2007/132353 (Becton Dickinson France) and GB 2 437 922 (Owen Mumford Ltd). These boot removers also have an outward-flaring base or collar.

SUMMARY OF THE INVENTION

It is an object of the present invention to provide apparatus comprising a booted syringe and a boot removal mechanism that is both easy to use and reliable, reducing the failure rate of assembled injection devices and helping to maintain sterility.

According to a first aspect of the present invention there is provided apparatus for loading into an injection device and comprising:
  a syringe having a syringe body, a needle and a boot providing a sterile cover for the needle; and
  a boot remover, the boot remover having a body for substantially enclosing the boot and a lip or lips projecting inwardly to engage a junction between the boot and the syringe body, the boot remover having, at its widest point, substantially the same outer dimension as, or a smaller outer dimension than, the syringe body, wherein the apparatus can be loaded into an injection device through an opening at a distal end of the device such that, when loaded, a portion of the boot remover projects through a proximal end of the device to facilitate removal of the boot remover and boot by a user.

Preferably, the projecting portion of the boot remover is provided with a gripping formation for assisting removal of the boot remover and boot by the user. Said gripping formation may be a waist or undercut to aid gripping by a user and/or to allow the grip to be engaged by a secondary boot removal tool held by the user.

In one embodiment of the invention, the boot remover may be formed as two substantially identical portions provided with complimentary interlocking features such that the identical portions can be placed around the boot and snapped together to cause the lip or lips to engage said junction.

The two substantially identical portions may be hingeably connected together.

In a second embodiment of the invention the boot remover may comprise a single moulded component provided with a slot extending in an axial direction along said body from said lip or lips, the slot being dimensioned to allow a boot to be loaded into the opening within the body in a transverse direction such that said lip or lips engage the junction between the boot and the syringe body.

The boot remover may be of a substantially rigid material, e.g. a rigid plastics material.

The boot remover is preferably dimensioned to allow the syringe and boot remover to be inserted through a casing part, preferably a distal or non-injection end, of an injection device. Preferably, the syringe is pre-filled.

According to a second aspect of the present invention there is provided an injection device comprising apparatus according to any one of the preceding claims, wherein the device further comprises means for assisting with the injection of medicament from the syringe.

The boot remover is dimensioned to have approximately the same width as the syringe body. Syringe bodies are typically cylindrical. The lip may project inwardly from an open end of said hollow body and is preferably configured to engage with the junction. The gripping formation or grip may extend axially from said body and may be configured to project outwardly through an open end of an injecting device.

Preferably, the boot remover is dimensioned to allow the syringe and the boot remover to be inserted through an opening in a distal (i.e. a non-injection) end of a casing part of the injection device.

It will be appreciated that the boot remover facilitates the removal of the boot from the syringe. The apparatus is configured to be loaded into an injection device. The junction may be at a proximal end of the syringe body. The outer dimension is preferably the diameter of a cylindrical body. A user may remove the boot from the syringe by holding and pulling on said grip.

The body of the boot remover is preferably hollow and preferably also cylindrical. As such, it will be appreciated that corresponding widths or diameters will translate to corresponding circumferences. Thus, the hollow body of the boot remover is proportioned to fit snugly over the boot and have substantially the same diameter or circumference as the syringe body.

Accordingly, the outer surface of the hollow body covering the boot is in substantially the same plane as the syringe body. The boot remover may extend over the junction (between the boot and the proximal end of the syringe body) so that the hollow body and the syringe body are substantially flush.

The circumference of the boot remover may vary along its length, particularly at the grip, which may even be flatter or oval in cross-section. However, the outer circumference of the boot remover, at its widest point, is substantially the same as the outer circumference of the syringe body. It therefore follows that the greatest outer diameter, found along the (axial) length, of the boot remover is substantially the same as that of the outer diameter of the syringe body.

It is therefore preferred that the greatest outer dimension or diameter of the boot remover is that of the hollow body at the junction between the boot and the proximal end of the syringe body.

The outer dimension or circumference of the boot remover at its widest point is preferably no more than 20%, preferably no more than 15%, preferably no more than 10%, preferably no more than 8% preferably no more than 6%, preferably no more than 4% or even no more than 2% greater than the outer dimension or circumference of the syringe body.

Alternatively, the outer dimension or circumference of the boot remover at its widest point is preferably no more than 20%, preferably no more than 15%, preferably no more than 10%, preferably no more than 8% preferably no more than 6%, preferably no more than 4% or even no more than 2% less than the outer dimension or circumference of the syringe body.

A range of between 95%-105% of the outer dimension or circumference of the syringe body is particularly preferred for the outer dimension or circumference of the boot remover at its widest point.

It will be appreciated that the above discussion of outer dimensions or circumferences also applies to the corresponding diameters of said parts.

Preferably, the widest point of the hollow body has the same outer diameter as the grip, i.e. are co-planar.

In a further aspect, the invention provides apparatus comprising:

a pre-filled syringe having a syringe body, a needle and a boot providing a sterile cover for the needle; and a boot remover for facilitating the removal of the boot from the syringe, the apparatus being configured to be loaded into an injection device, and the boot removal means comprising:

a hollow cylindrical body for substantially enclosing a boot;

a lip or lips projecting inwardly from an open end of said hollow body and configured to engage with a junction between the boot and a proximal end of the syringe body; and a grip extending axially from said hollow body and configured to project outwardly through an open end of an injecting device, the boot removal means, at its widest point, having substantially the same outer diameter as the syringe body, wherein a user can remove the boot from the syringe by holding and pulling on said grip.

In a still further aspect, the invention provides apparatus for facilitating the removal of a boot from a pre-filled syringe, the boot providing a sterile cover for a needle of the syringe, and the syringe being configured to be loaded into an injection device, the apparatus comprising:

a hollow cylindrical body for substantially enclosing a boot;

a lip or lips projecting inwardly from an open end of said body and configured to engage with a junction between the boot and a proximal end of the syringe body, the lip or lips being substantially rigid with respect to said body; and a grip extending axially from said body and configured to project outwardly through an open end of an injecting device, wherein a user can remove the boot from a syringe by holding and pulling on said grip.

DETAILED DESCRIPTION

WO 2007/036676 (supra) allows the boot and the syringe to be inserted into the distal or non-injection end of the device. However, it does not allow the boot remover to be first engaged with the boot, prior to insertion of the boot (plus syringe and boot remover) into the injection device housing. A disadvantage with this arrangement is that the user cannot be certain that the boot remover has properly engaged with the boot until the device comes to be used. However, the present invention allows the boot remover to be engaged with the boot, for instance by a supplier, and then provided to the user. This ensures peace of mind and reduces the number of assembly steps required. This also has the advantage of helping to maintain the sterility of the apparatus.

Lee et al (US 2007/0167916 A1) relates to an outer barrel for a safety syringe. The barrel is composed of two halves and serves to protect the needle when no boot is present. The barrel cannot be used to remove the boot itself. A safety device to prevent needle prick is disclosed in JP 2000116777 A (Mitsubishi Pencil Co.), comprising a piece of board, with suitable recesses, such that the board can be folded in half to enclose an exposed needle. GB 2 414 401 A (Cilag AG International) provides an injection device comprising a housing, the housing being open along one side. The device seeks to address the problem of damage caused to flanges on syringe bodies by injection device drive springs.

Neither WO 2007/047200, WO 2007/132353 nor GB 2 437 922 (supra) allow the boot remover to be engaged with the boot and then inserted into the injection device. This is because their boot removers are flared outwards beyond the diameter of the injection device housing. Lee et al (US 2007/0167916 A1), JP 2000116777 A and GB 2 414 401 A do not disclose boot removers at all.

The boot remover will now be described that enables the easy and reliable removal of a boot or sheath covering a needle of a pre-filled syringe. As has already been outlined above, an assembler of injection devices (e.g. auto-injectors and the like) will obtain pre-filled syringes from a supplier. It will be appreciated that any syringe may be used in the present apparatus, so the boot remover will have to be sized accordingly.

Figure 1:
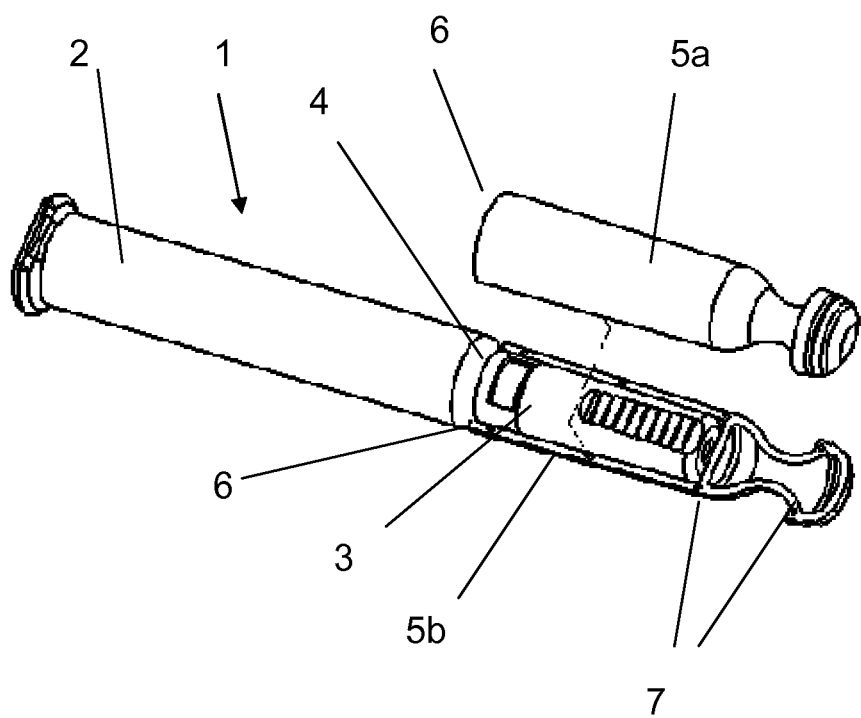
FIG. 1 illustrates apparatus according to a first embodiment of the present invention, the apparatus being assembled about a boot of a pre-filled syringe and comprising the boot remover.

A typical syringe comprises a body containing the medicament, a plunger located within the body and extending outwardly therefrom, and a hypodermic needle coupled to the opposite end of the body. A rubber or plastics boot covers the needle and seals around a shoulder portion of the body. FIG. 1 illustrates such a syringe 1 with body 2 and boot 3. At the junction between the boot 3 and the distal end of the body 2, a small axial gap 4 exists.

FIG. 1 also shows two substantially identical boot remover "halves" 5a and 5b. Each half is moulded as a single piece from a rigid plastics material. FIG. 1 shows a lower half 5b placed around the underside of the syringe boot 2. Each of the proximal ends of the halves are provided with an inwardly projecting lip 6, extending around the circumference of the end. In the assembly state of FIG. 1, the lip 6 of the lower half 5b engages with the gap 4 formed between the boot 3 and the end of the syringe. During assembly, the upper half 5a is pressed down onto the lower half 5b such that a series of dimples and cooperating projections 7, formed along the lengths of the halves, snap together, causing the boot remover to completely surround the boot.

Figure 2:
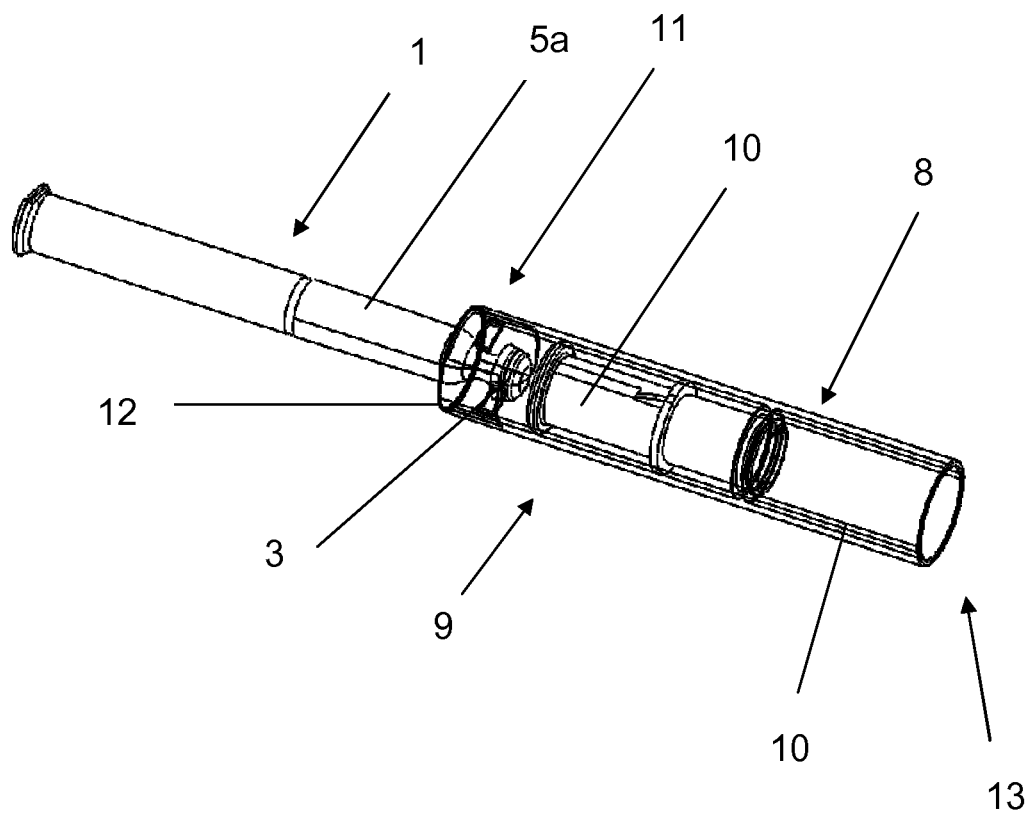
FIG. 2 illustrates an intermediate stage in the assembly of an injection device comprising the apparatus of FIG. 1.
Figure 3:
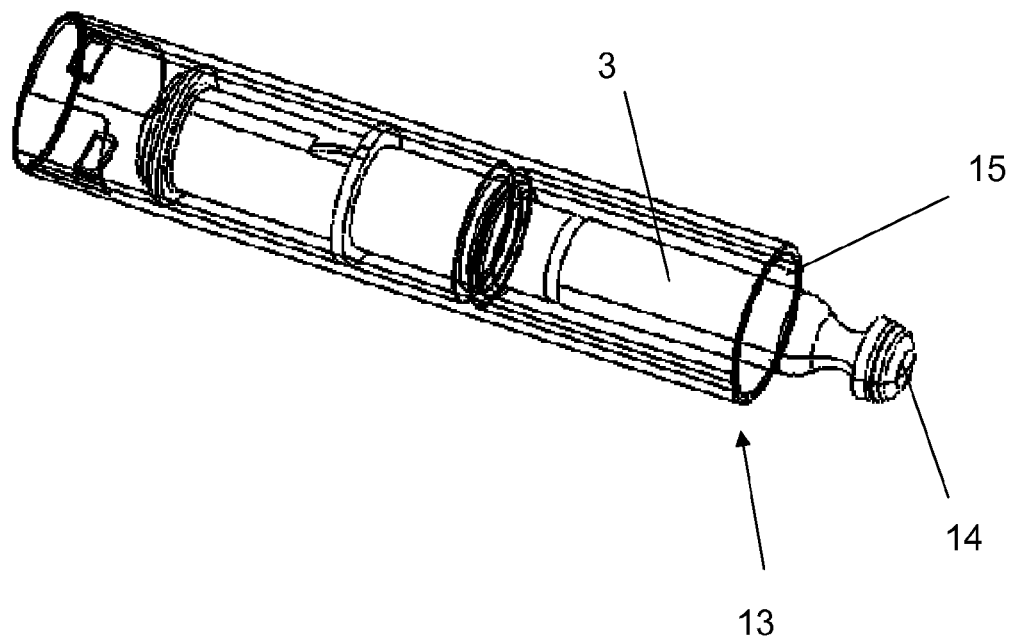
FIG. 3 illustrates an assembled state of the injection device of FIG. 2.

FIG. 2 illustrates the syringe 1 being inserted into the casing 8 of an injection device 9 having a housing 10. The syringe, engaged with the boot remover is inserted into the non-injection end 11 of the device 9 via opening 12. It will be appreciated that the injection end of the device 13 is that closest to the needle when assembly of the device, apparatus (the boot remover and the booted syringe) is completed and ready for use. Therefore, the distal/non-injecting end 11 is the opposite end of the device from the proximal/injection end 13. The injection device is not shown in any great detail, except for an internal mechanism 12. The outer diameters of the syringe 1 and the boot 3 are such that the syringe can be inserted through the casing from opening 12 in the casing until the syringe arrives at some lower stop. This position is illustrated in FIG. 3. It can be seen from the Figure that a grip or knob 14 formed at the end of the boot 3 projects through an opening 15 at the injection end 13 of the casing. The grip 14 is undercut to assist a user in grasping the grip. Although not illustrated in the Figures, the end 11 of the casing through which the syringe is inserted is subsequently closed to secure the syringe in place.

Figure 4:
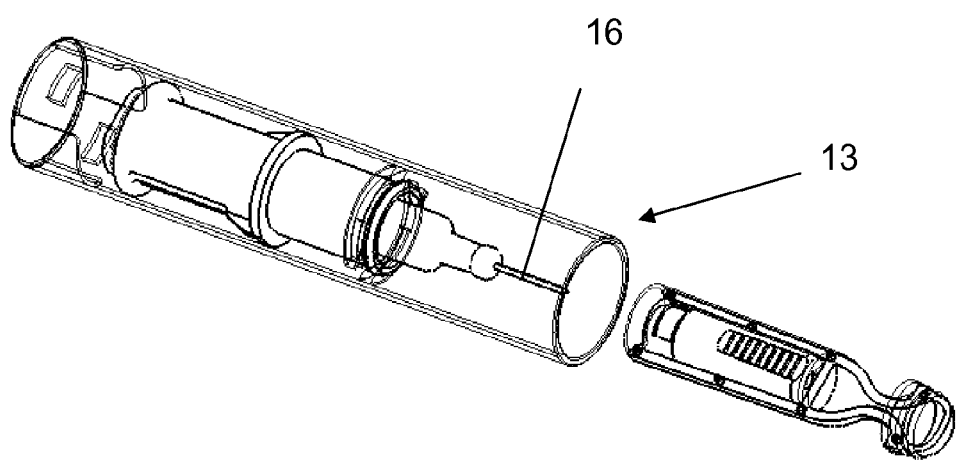
FIG. 4 illustrates a step of removing the boot remover, and captured boot, from the assembled device of FIG. 3.

FIG. 4 illustrates in turn the injection device following removal of the cap by a user, i.e. by grasping and pulling on the grip 14. The needle 16 is then exposed although, at this stage and prior to firing the device, it remains within the casing.

Figure 5:
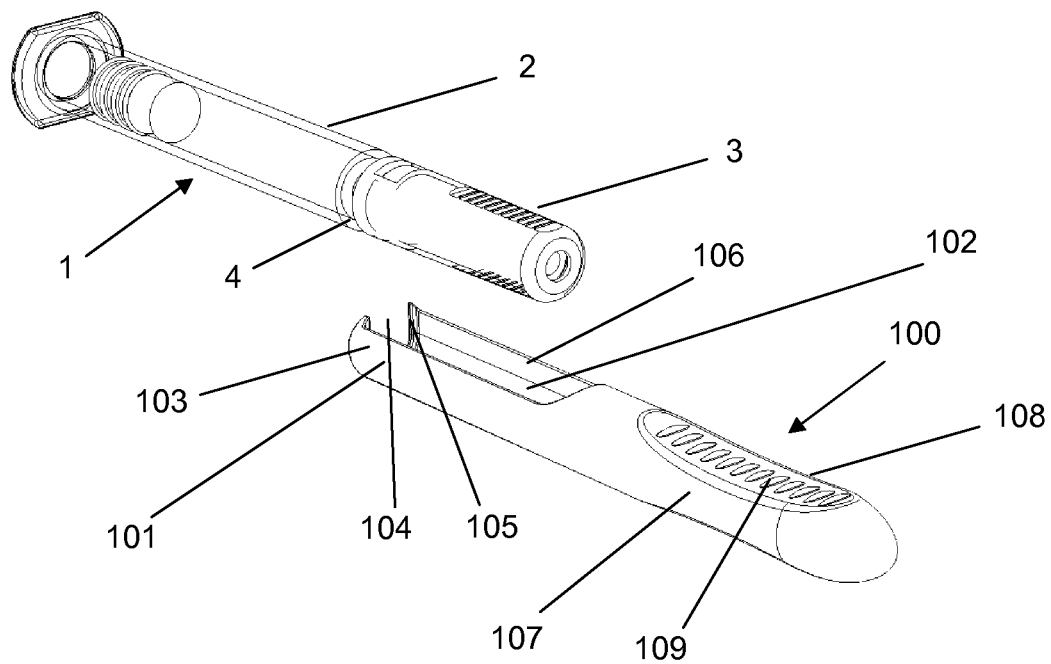
FIG. 5 illustrates apparatus according to a second embodiment of the present invention, the apparatus being assembled about a boot of a pre-filled syringe and comprising the boot remover.

FIG. 5 illustrates an alternative boot remover 100. The syringe 1 is identical to the syringe described above and like reference numerals are used to identify its various components. The boot remover 100 is formed as a single, moulded plastics member. A body portion 101 is generally cylindrical, having a hollow interior space 102. A proximal end 103 of the body is provided with an opening 104. A lip 105 extends around the circumference of the opening 104, projecting slightly inwards. A slot 106 extends from the opening 105, to a point about midway along the length of the boot remover 100. At this point, the body 101 extends into a grip 107 which may be hollow or solid. The grip 107 narrows slightly into a waist section 108. The outer surfaces of the waist are provided with ridges 109 to improve a user's grip.

Figure 6:
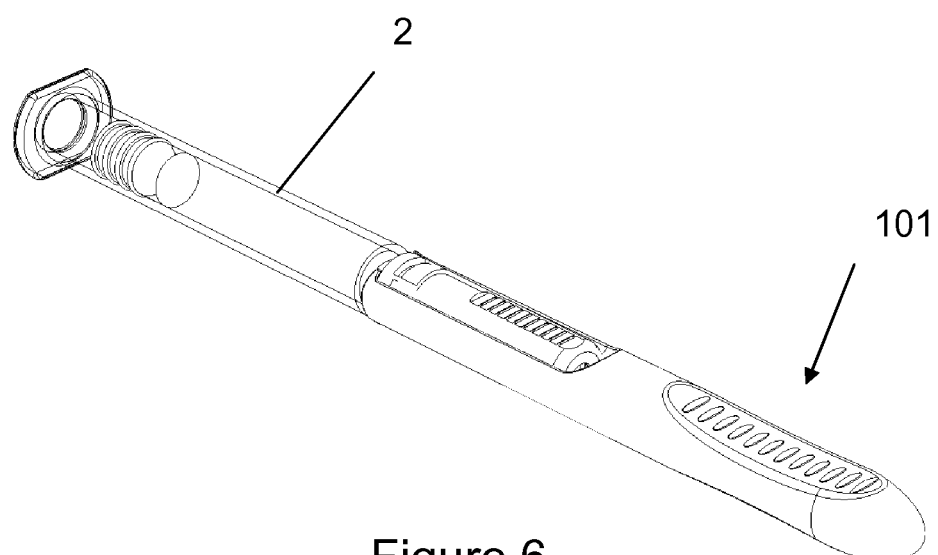
FIG. 6 illustrates the apparatus of FIG. 5 following loading of a pre-filled syringe.

It will be appreciated from FIG. 5 that the boot 3 of the syringe 1 can be pressed through the slot 106 provided in the body, into the interior space 102, providing that the width of the slot is greater than the narrowed diameter of the junction between the syringe end and the boot. In some cases, the width of the slot may be slightly less than this diameter, so that once pressed into the body the boot (and syringe) are held in place. However, this may not be necessary as, once the syringe and boot remover are installed in the injection device, the boot is prevented from falling out of the boot remover by the interior configuration of the injection device. FIG. 6 illustrates the syringe following pressing of the boot into the boot remover.

As with the apparatus described with reference to FIGS. 1 to 4, the syringe and boot remover are subsequently loaded into an injection device, by insertion through a loading opening in the non-injection end of the device. Once installed, the grip 107 projects through an injection end opening of the device, allowing a user to remove the remover by gripping and pulling on the grip 107.

Figure 7:
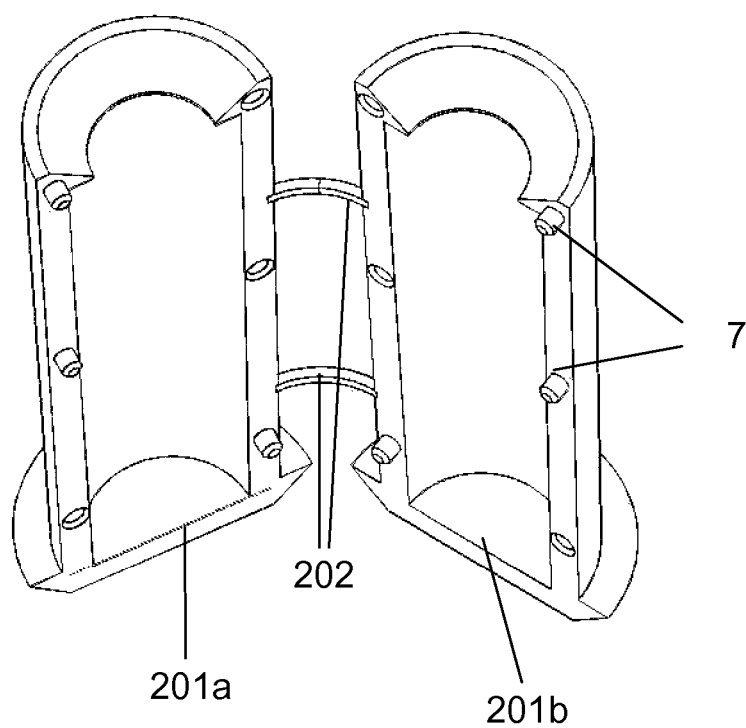
FIG. 7 illustrates a further embodiment of a boot remover.

FIG. 7 illustrates a further embodiment of a boot remover 200. This is similar to the apparatus of FIG. 1, except that the two halves of the device 201a, 201b are hingeably coupled together along one side by a pair of hinges 202. During assembly, a first of the halves 201a is placed beneath the syringe body, following which the second half 201b is folded over and snapped into place. Projections 7 are also shown.

It will be appreciated by the person of skill in the art that various modifications may be made to the above described embodiments without departing from the scope of the invention.

The invention claimed is:

1. A treatment apparatus comprising:
   an injection device having proximal and distal ends with a hole at the distal end;
   a syringe having a syringe body, a needle and a boot providing a sterile cover for the needle; and
   a boot remover, the boot remover having a body substantially enclosing the boot and a lip or lips projecting inwardly to engage a junction between the boot and the syringe body, the boot remover having, at its widest point, substantially the same outer dimension as, or a smaller outer dimension than, the syringe body, wherein the syringe and boot remover are configured to be loaded together into the injection device through the opening at the distal end of the injection device such that, when loaded, a portion of the boot remover projects through the proximal end of the injection device to facilitate removal of the boot remover and boot by a user.

2. The apparatus of claim 1, wherein the projecting portion of the boot remover is provided with a gripping formation for assisting removal of the boot remover and boot by the user.

3. The apparatus of claim 2, said gripping formation comprising a waist or undercut to aid gripping by a user and/or to allow the gripping formation to be engaged by a secondary boot removal tool held by the user.

4. The apparatus of claim 1, the boot remover being formed as two substantially identical portions provided with complimentary interlocking features such that the identical portions can be placed around the boot and snapped together to cause the lip or lips to engage said junction.

5. The apparatus of claim 4 wherein said two substantially identical portions are connected together using a hinged connection.

6. The apparatus of claim 1, the boot remover comprising a single moulded component provided with a slot extending in an axial direction along said body from said lip or lips, the slot being dimensioned to allow a boot to be loaded into the opening within the body in a transverse direction such that said lip or lips engage the junction between the boot and the syringe body.

* * * * *